United States Patent [19]

Chinnock et al.

[11] Patent Number: 5,056,902

[45] Date of Patent: Oct. 15, 1991

[54] MAGNETICALLY COUPLED LENS ACTUATOR

[75] Inventors: Randal B. Chinnock, North Reading; Norman J. Dionne, Arlington, both of Mass.

[73] Assignee: Smith & Nephew Dyonics, Inc., Andover, Mass.

[21] Appl. No.: 514,119

[22] Filed: Apr. 25, 1990

[51] Int. Cl.$^5$ .......................... G02B 7/04; G02B 7/08; G02B 23/24

[52] U.S. Cl. ........................................ 359/503; 128/4; 359/513; 359/823; 359/903

[58] Field of Search ............... 350/574, 255, 582, 589, 350/518, 564, DIG. 3; 128/4

[56] References Cited

U.S. PATENT DOCUMENTS

| | | |
|---|---|---|
| 3,900,021 | 8/1975 | Makepeace et al. . |
| 3,917,394 | 11/1975 | Sturdevant .......................... 350/255 |
| 4,076,018 | 2/1978 | Heckele .................... 128/6 |
| 4,272,161 | 6/1981 | Feinbloom . |
| 4,318,395 | 3/1982 | Tawara . |
| 4,378,952 | 4/1983 | Siegmund . |
| 4,413,278 | 11/1983 | Feinbloom . |
| 4,478,212 | 10/1984 | Asano . |
| 4,525,830 | 6/1985 | Montagu et al. . |
| 4,569,333 | 2/1986 | Bel et al. . |
| 4,611,888 | 10/1986 | Prenovitz et al. . |
| 4,625,714 | 12/1986 | Toyota et al. . |
| 4,685,450 | 8/1987 | Collins et al. . |
| 4,697,894 | 10/1987 | Takamura et al. .................. 350/574 |
| 4,740,058 | 4/1988 | Hori et al. . |
| 4,756,304 | 7/1988 | Watanabe . |
| 4,801,197 | 1/1989 | Minami . |
| 4,807,594 | 2/1989 | Chatenever . |
| 4,844,071 | 7/1989 | Chen et al. . |
| 4,862,199 | 8/1989 | Centkowski . |

FOREIGN PATENT DOCUMENTS

| | | |
|---|---|---|
| 970298 | 9/1958 | Fed. Rep. of Germany ...... 350/255 |
| 195339 | 12/1982 | Japan .................................... 350/255 |
| 1389747 | 7/1986 | U.S.S.R. . |
| 430826 | 12/1933 | United Kingdom . |

*Primary Examiner*—Jon W. Henry
*Attorney, Agent, or Firm*—Fish & Richardson

[57] ABSTRACT

A lens surrounded by a protective chamber is focused by utilizing a magnetic field to adjust the position of the lens within the chamber. By using a magnetic field to adjust the lens position, it is not necessary to pass a mechanical device through the surface of the chamber, thereby allowing the chamber to be completely sealed to prevent contaminants from contacting the lens.

64 Claims, 1 Drawing Sheet

U.S. Patent
Oct. 15, 1991
5,056,902
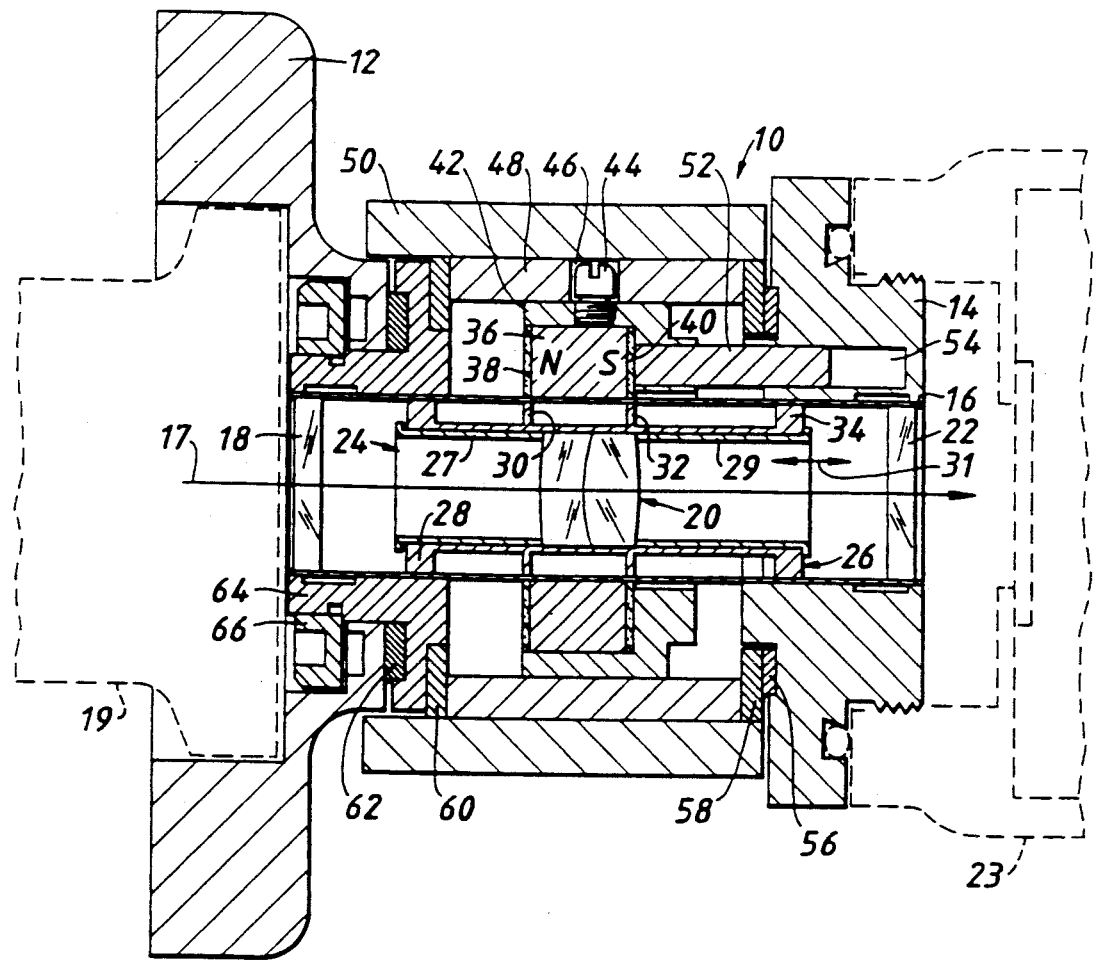

MAGNETICALLY COUPLED LENS ACTUATOR

FIELD OF THE INVENTION

This invention is related to magnetic coupling.

BACKGROUND OF THE INVENTION

Physicians frequently use optical devices to facilitate examining an area that might otherwise be difficult to observe. For example, when performing arthroscopic knee surgery, a surgeon inserts an arthroscope through a small incision in the patient's leg and manipulates the arthroscope to various areas of interest. The arthroscope uses optical fibers to illuminate the area of interest inside the patient's knee and an optical assembly for picking up an image and transmitting it either for direct observation by the surgeon or to a video camera for display on a TV monitor. Because the surgeon will be moving the arthroscope to various areas of interest throughout the procedure, the distance between the arthroscope's distal tip and the area of interest will vary. It is therefore necessary to provide some mechanism for focusing the image picked up by the arthroscope in order to produce a high quality view on the monitor. Such a focusing mechanism typically consists of at least one focusing lens whose position can be adjusted by the surgeon during the procedure. The focusing lens is placed in a chamber in order to minimize the intrusion of contaminants and to prevent it from fogging during the procedure. The chamber also protects the lens when the device is being cleaned and sterilized between surgical procedures. Cleaning is typically achieved by washing in soaps and disinfecting solutions. Sterilization is accomplished usually by exposure to ethylene oxide gas or by steam autoclaving (the application of superheated steam under high pressure to the medical instrument). Since it is necessary to move the focusing lens within the chamber to achieve a desired focus, a mechanical adjustment mechanism extends within the sealed chamber and contacts the lens (or some structure supporting the lens) to enable the surgeon to manually move the lens. The point at which the mechanism penetrates the chamber must be sealed as tightly as possible to keep the lens clean and fog-free.

SUMMARY OF THE INVENTION

In the invention, a lens surrounded by a protective chamber is focused by utilizing a magnetic field to adjust the position of the lens within the chamber. By using a magnetic field to adjust the lens position, it is not necessary to pass a mechanical device through the surface of the chamber, thereby allowing the chamber to be completely sealed to prevent contaminants from contacting the lens.

In general, in one aspect, the invention features adjusting the position of a lens to thereby adjust the focus of light passing through the lens. The lens is surrounded by a sealed protective chamber. The chamber includes a window to permit light to enter the chamber and the lens; an actuator held inside the chamber and movable with respect to the chamber, the actuator being arranged to cause motion of the lens when the actuator is moved; and an element held outside the chamber and ferromagnetically coupled to the actuator through a surface of the chamber, the element being movable relative to the chamber to cause movement of the actuator to thereby adjust the position of the lens.

The invention also generally features a method for moving a focusing lens having a protective chamber surrounding the lens, the chamber including a window to permit light to enter the chamber and the lens, the chamber comprising an actuator positioned inside the chamber and arranged to cause motion of the lens when the actuator is moved, the method comprising moving an element that is ferromagnetically coupled to the actuator and positioned outside the chamber to cause the actuator to move thereby adjusting the position of the lens.

In preferred embodiments, the element comprises a magnet and the actuator is ferromagnetic to thereby define a closed flux path for flux generated by the magnet. The actuator comprises two projections which form part of the flux path, and which are in sliding contact with the inner surface of the chamber. Two ferromagnetic washers are positioned adjacent to each pole of the magnet, each of the washers being aligned with one of the projections on the actuator. The washers are configured to conduct flux radially. The magnet is supported by a magnet support that has a stabilization member to restrict the movement of the magnet. The magnet is preferably a ring-shaped permanent magnet and can be moved in a direction that is parallel to an axis of the chamber. Alternatively, the actuator and the element can both be magnets, or the element can be ferromagnetic and the actuator can be a magnet.

The chamber is preferably cylindrical, non-magnetic and is sealed at each of its ends by a window through which light may pass. The curved surface of the cylindrical chamber is continuous and free of apertures through which debris or other contaminants could pass. The sealed chamber prevents motion from being transmitted mechanically through the wall of the chamber.

The apparatus may be a medical device such as an endoscope coupler for coupling an endoscope to another device (e.g., a video monitor). The apparatus may also be, e.g., a video arthroscope, which is designed to couple directly to a video camera without an auxiliary coupler; a camera with integral focusing optics; a beam splitter type coupler, which provides simultaneous viewing of an image through an occular as well as a video system; or couplers designed to permit photography through endoscopes. The invention may also be a device which moves an apparatus contained within a sealed chamber other than a lens.

Other features and advantages of the invention may become apparent from the following detailed description, and from the claims.

BRIEF DESCRIPTION OF THE DRAWING

The sole figure is a cross sectional view of an endoscope coupler.

DETAILED DESCRIPTION OF THE PREFERRED EMBODIMENT

STRUCTURE

Referring to the figure, endoscope coupler 10 includes a front housing 12 and a rear housing 14. The apparatus may be a medical device such as an endoscope coupler for coupling an endoscope to another device (e.g. a video monitor). Front housing 12 includes a spring operated variable split ring clamp that can attach to endoscopes of various diameters. Light 17 from an endoscope 19 enters a sealed nonmagnetic cylindrical tube 16 through a front window 18, passes through focusing lenses 20 and exits tube 16 through a rear window 22 and into a video head assembly 23 for viewing on a monitor. Lenses 20 are mounted in a support structure 24 that includes a generally cylindrical permeable steel, ferromagnetic support 26 and a pair of nonmagnetic tubes 27, 29. Ferromagnetic support 26 includes radial projections 28, 30, 32 and 34, each of which is in sliding contact with the inner surface of tube 16 to allow ferromagnetic support 26 to slide freely (arrow 31) within tube 16 thereby moving lenses 20 toward and away from front window 18 and the source of the light for focusing. Projections 28 and 34 are thicker than projections 30, 32 to provide stable supporting surfaces for support structure 24 within tube 16. Windows 18, 22 are sealed to tube 16 either by adhesives or by a solder or braze connection. Tube 16 is fixed at opposite ends to housing 12, 14 either by adhesives or by mechanical means such as an interference press fit, threads or a solder or braze connection.

A ring shaped permanent magnet 36 surrounds tube 16 and has retaining permeable steel flux conducting washers 38, 40 adjacent to its north (N) and south (S) poles, respectively. The inner diameter of magnet 36 is slightly larger than the outer diameter of tube 16 so that magnet 36 may slide freely along tube 16. The length of magnet 36 together with the two retaining washers 38, 40 matches the distance spanned by the two projections 30, 32. Magnet 36 and washers 38, 40 are supported by a support structure 42 which receives a screw 44 in its radially outermost surface. The support structure may be attached to magnet 36 by adhesives, threads, interference press or a retaining ring. The head of screw 44 fits within a helical groove 46 formed in a cylindrical focusing sleeve 48. Focusing sleeve 48 is mounted within and may be rotated by rotating a cylindrical focusing ring 50 attached to sleeve 48 by adhesives or threads. An antirotation or stabilizing rod 52 is secured at one end to magnet support 42 by a press fit and at its other end is received in a hole 54 formed in housing 14. Endoscope coupler 10 also includes a wave spring 56, floating washers 58, 60 and 62, support 64 and nut 66. The washers are made of a dimensionally stable material with low coefficient of friction, such as bronze or a polyamide-imide plastic.

Operation

In operation, light representing an image that passes through tube 16 is focused onto an imaging sensor (not shown) in head assembly 23 by lenses 20, the focus being adjustable by moving lenses 20 toward and away from the imaging sensor. To achieve the adjustment, focusing ring 50 is rotated to thereby rotate focusing sleeve 48. The head of screw 44 will move within helical groove 46 as focusing sleeve 48 is rotated and will therefore move either toward front housing 12 or toward rear housing 14, depending on the direction of rotation of focusing ring 50. The movement of screw 44 will cause magnet support 42, magnet 36, and washers 38, 40 to move outside of tube 16. Stabalization rod 52 stabilizes magnet 36 and prevents magnet 36 from rotating with focusing sleeve 48. Since support 26 is ferromagnetic, a flux path is established between the north and south poles of magnet 36 via washers 38, 40, projections 30, 32, and the tubular part of support 34. As a result, as magnet 36 moves, lens support 24 and lenses 20 will also move, thereby adjusting the focus of the image passing through tube 16.

The washers function as bearings for the entire assembly. This prevents "cocking" or binding and prevents abrasive contact between the magnet assembly and tube 16. Wave spring 56 functions to prevent "endplay" (i.e., axial movement). The primary sliding surfaces are the surfaces of washers 58 and 60.

Because focus is achieved without the need to extend any mechanical components through the surface of sealed tube 16, no debris or steam can enter the tubes in which the lenses are housed. Conventional focusing devices use a direct mechanical connection between the lenses and some external adjustment such as the above described focusing ring. It is therefore necessary to have apertures in the chamber that contains the lenses to admit the mechanical components of the adjustment mechanism. Although the apertures are typically sealed as well as possible, dirt, disinfecting solutions and water vapor are still sometimes able to penetrate into the chamber causing the lenses to become dirty or fogged, degrading performance of the device, and necessitating a difficult and time consuming cleaning of the lenses which is typically done by the manufacturer, making the device unavailable to the physician. In the present invention, the lenses will remain dirt and fog free throughout the surgical procedure. Furthermore, when the device is cleaned and sterilized between surgical operations such as by autoclaving, the steam will not be able to penetrate into the chamber thereby preventing the lenses from fogging.

Other embodiments are within the following claims. For example, instead of using a single lens assembly and moving the lens axially to achieve the desired focus, multiple lenses can be selectively moved into the path of the light passing through the chamber, with each lens providing a different predetermined focus.

We claim:

1. An apparatus for adjusting the position of a lens, comprising:
   a sealed chamber surrounding said lens, said chamber including a window to permit light to enter said chamber and said lens;
   an actuator held inside said chamber, said actuator being movable with respect to said chamber, said actuator being arranged to cause motion of said lens when said actuator is moved, said actuator having a plurality of projections that extend radially toward an inner surface of said chamber to provide a spacing between said actuator and said inner surface that is less at said projections than in a region of said actuator disposed between said projections; and
   an element held outside said chamber and ferromagnetically coupled to at least some of said projections of said actuator through a surface of said chamber, said element being movable relative to said chamber to cause movement of said actuator to thereby adjust the position of said lens.

2. The apparatus of claim 1 wherein said actuator or said element comprises a magnet.

3. The apparatus of claim 1 wherein said actuator or said element define a closed flux path.

4. The apparatus of claim 3 wherein said projections define part of said flux path and are in sliding contact with said inner surface of said chamber.

5. An apparatus for adjusting the position of a lens, comprising:

a sealed chamber surrounding said lens, said chamber including a window to permit light to enter said chamber and said lens;

an actuator held inside said chamber, said actuator being movable with respect to said chamber, said actuator being arranged to cause motion of said lens when said actuator is moved;

an element comprising a magnet held outside said chamber and ferromagnetically coupled to said actuator through a surface of said chamber, said element being movable relative to said chamber to cause movement of said actuator to thereby adjust the position of said lens;

said actuator comprising projections which define part of a closed flux path between said actuator and said element, said projections being in sliding contact with an inner surface of said chamber; and two ferromagnetic washers, respectively positioned adjacent the poles of said magnet and respectively aligned with said projections.

6. The apparatus of claim 5 wherein said washers are configured to conduct flux radially.

7. The apparatus of claim 1 wherein said element comprises a magnet and a magnet support secured to said magnet, said magnet support including a stabilization member to restrict movement of said magnet.

8. The apparatus of claim 1 wherein said chamber is cylindrical.

9. The apparatus of claim 8 wherein said cylindrical chamber is sealed at each of its ends by a window through which said light may pass.

10. The apparatus of claim 8 wherein the curved surface of said cylindrical chamber is continuous and free of apertures through which debris or other contaminants could pass.

11. The apparatus of claim 1 wherein said apparatus further comprises a medical device.

12. The apparatus of claim 1 wherein said chamber is sealed such that motion cannot be transmitted mechanically through the wall of said chamber.

13. The apparatus of claim 1 wherein the surface of said chamber is continuous and free of apertures through which debris or other contaminants could pass.

14. The apparatus of claim 2 wherein said element is configured to be moved in a direction parallel to an axis of said chamber.

15. The apparatus of claim 5 wherein said magnet is ring-shaped.

16. The apparatus of claim 2 wherein said magnet comprises a permanent magnet.

17. The apparatus of claim 1 wherein said chamber is non-magnetic.

18. The apparatus of claim 2 wherein said actuator is ferromagnetic.

19. The apparatus of claim 1 wherein said actuator comprises a magnet.

20. The apparatus of claim 1 wherein said lens is configured to move along an optical axis on which said lens lies.

21. An apparatus for adjusting the position of a lens along an optical axis on which the lens lies, comprising:

a cylindrical chamber surrounding said lens, said chamber being sealed in a manner that prevents motion from being transmitted mechanically through the wall of said chamber, said chamber including a window to permit light to enter said chamber and pass through said lens;

a ferromagnetic actuator held inside said chamber and supporting said lens, said actuator being movable with respect to said chamber to thereby cause motion of said lens, said actuator having a plurality of projections that extend radially toward an inner surface of said chamber to provide a spacing between said actuator and said inner surface that is less at said projections than in a region of said actuator disposed between said projections; and a ring-shaped magnet surrounding said chamber and ferromagnetically coupled to at least some of said projections of said actuator via a surface of said chamber, said magnet being movable relative to said chamber to cause movement of said ferromagnetic actuator to thereby adjust the focus of said light passing through said lens.

22. An endoscope coupler for coupling an endoscope to a viewing device, said coupler comprising:

a lens;

a sealed chamber surrounding said lens, said chamber including a window to permit light to enter said chamber and said lens;

an actuator held inside said chamber, said actuator being movable with respect to said chamber, said actuator being arranged to cause motion of said lens when said actuator is moved, said actuator having a plurality of projections that extend radially toward an inner surface of said chamber to provide a spacing between said actuator and said inner surface that is less at said projections than in a region of said actuator disposed between said projections; and an element held outside said chamber and ferromagnetically coupled to at least some of said projections of said actuator through a surface of said chamber, said element being movable relative to said chamber to cause movement of said actuator to thereby adjust the position of said lens.

23. The apparatus of claim 22 wherein said actuator or said element comprises a magnet.

24. The apparatus of claim 21 wherein said actuator defines a closed flux path.

25. The apparatus of claim 24 wherein said projections define part of said flux path and are in sliding contact with said inner surface of said chamber.

26. An endoscope coupler for coupling an endoscope to a viewing device, said coupler comprising:

a lens;

a sealed chamber surrounding said lens, said chamber including a window to permit light to enter said chamber and said lens;

an actuator held inside said chamber, said actuator being movable with respect to said chamber, said actuator being arranged to cause motion of said lens when said actuator is moved;

an element comprising a magnet held outside said chamber and ferromagnetically coupled to said actuator through a surface of said chamber, said element being movable relative to said chamber to cause movement of said actuator to thereby adjust the position of said lens;

said actuator comprising projections which define part of a closed flux path between said actuator and said element, said projections being in sliding contact with an inner surface of said chamber; and two ferromagnetic washers, respectively positioned adjacent to the poles of said magnet and respectively aligned with said projections.

27. The apparatus of claim 26 wherein said washers are configured to conduct flux radially.

28. The apparatus of claim 22 wherein said element comprises a magnet and a magnet support secured to said magnet, said magnet support including a stabilization member to restrict movement of said magnet.

29. The apparatus of claim 22 wherein said chamber is cylindrical.

30. The apparatus of claim 29 wherein said cylindrical chamber is sealed at each of its ends by a window through which said light may pass.

31. The apparatus of claim 29 wherein the curved surface of said cylindrical chamber is continuous and free of apertures through which debris or other contaminants could pass.

32. The apparatus of claim 22 wherein said chamber is sealed such that motion cannot be transmitted mechanically through the wall of said chamber.

33. The apparatus of claim 22 wherein the surface of said chamber is continuous and free of apertures through which debris or other contaminants could pass.

34. The apparatus of claim 22 wherein said element is configured to be moved in a direction parallel to an axis of said chamber.

35. The apparatus of claim 26 wherein said magnet is ring-shaped.

36. The apparatus of claim 23 wherein said magnet comprises a permanent magnet.

37. The apparatus of claim 22 wherein said chamber is non-magnetic.

38. The apparatus of claim 23 wherein said actuator is ferromagnetic.

39. The apparatus of claim 22 wherein said actuator comprises a magnet.

40. The apparatus of claim 22 wherein said lens is configured to move along an optical axis on which said lens lies.

41. A method for moving a focusing lens having a chamber surrounding said lens, said chamber including a window to permit light to enter said chamber and said lens, said method comprising
providing an actuator positioned inside said chamber and arranged to cause motion of said lens when said actuator is moved, said actuator having a plurality of projections that extend radially toward an inner surface of said chamber to provide a spacing between said actuator and said inner surface that is less at said projections than in a region of said actuator disposed between said projection, and
moving an element that is ferromagnetically coupled to at least some of said projections of said actuator and positioned outside said chamber to cause said actuator to move thereby adjusting the position of said lens to adjust the focus of the light.

42. The method of claim 41 wherein said actuator or said element comprises a magnet.

43. The method of claim 41 wherein said actuator and said element define a closed flux path.

44. The method of claim 43 wherein said projections define part of said flux path and are in sliding contact with said inner surface of said chamber.

45. A method for focusing a lens having a chamber surrounding said lens, said chamber including a window to permit light to enter said chamber and said lens, said method comprising
providing an actuator positioned outside said chamber and arranged to cause motion of said lens when said actuator is moved, said actuator comprising projections that are in sliding contact with an inner surface of said chamber, and
moving an element that is ferromagnetically coupled to said actuator through a closed flux path that includes said projections and positioned outside said chamber to cause said actuator to move thereby adjusting the position of said lens to adjust the focus of the light, said element comprising a magnet and wherein a ferromagnetic washer is positioned adjacent to each of the poles of said magnet, such that said washers are aligned with said projections.

46. The method of claim 45 wherein said washers conduct flux radially.

47. The method of claim 41 wherein said element comprises a magnet and a magnet support secured to said magnet, said magnet support including a stabilization member to restrict movement of said magnet.

48. The method of claim 41 wherein said chamber is cylindrical.

49. The method of claim 48 wherein said cylindrical chamber is sealed at each of its ends by a window through which said light may pass.

50. The method of claim 48 wherein the curved surface of said cylindrical chamber is continuous and free of apertures through which debris or other contaminants could pass.

51. The method of claim 41 wherein said lens is used to focus light from an endoscope.

52. The method of claim 41 wherein said chamber is sealed such that motion cannot be transmitted mechanically through the wall of said chamber.

53. The method of claim 41 wherein the surface of said chamber is continuous and free of apertures through which debris or other contaminants could pass.

54. The method of claim 42 wherein said element can be moved in a direction parallel to an axis of said chamber.

55. The method of claim 45 wherein said magnet is ring-shaped.

56. The method of claim 42 wherein said magnet comprises a permanent magnet.

57. The method of claim 41 wherein said chamber is non-magnetic.

58. The method of claim 42 wherein said actuator is ferromagnetic.

59. The method of claim 41 wherein said actuator comprises a magnet.

60. The method of claim 41 wherein said lens moves along an optical axis on which said lens lies.

61. A method for focusing light transmitted from an endoscope to a viewing apparatus such as a camera, the light passing through a lens having a chamber surrounding said lens, said chamber including a window to permit light to enter said chamber and said lens, said method comprising
providing an actuator positioned inside said chamber and arranged to cause motion of said lens when said actuator is moved, said actuator having a plurality of projections that extend radially toward an inner surface of said chamber to provide a spacing between said actuator and said inner surface that is less at said projections than in a region of said actuator disposed between said projections, and
moving an element that is ferromagnetically coupled to at least some of said projections of said actuator and positioned outside said chamber to cause said actuator to move thereby adjusting the position of said lens to adjust the focus of the light.

62. The method of claim 1 wherein said actuator further comprises second radially extending projections each one of which is axially spaced from one of the first mentioned projections, said second projections being in sliding contact with said inner surface of said chamber.

63. The method of claim 62 wherein said second projections each has an axial extent that exceeds an axial extent of each of said first mentioned projections.

64. The method of claim 62 wherein said second projections provide a spacing between said actuator and said inner surface of said chamber that is less at said second projections than in regions of said actuator disposed between said second projections and said first mentioned projections.

* * * * *

UNITED STATES PATENT AND TRADEMARK OFFICE
CERTIFICATE OF CORRECTION

PATENT NO.   : 5,056,902
DATED        : October 15, 1991
INVENTOR(S)  : Randal B. Chinnock and Norman J. Dionne It is certified that error appears in the above-identified patent and that said Letters Patent is hereby corrected as shown below:

```
Column 9, line 3: Replace "method" with
                  --apparatus--;

Column 10, line 1: Replace "method" with
                   --apparatus--;
           line 4: Replace "method" with
                   --apparatus--.
```

Signed and Sealed this

Eighth Day of June, 1993

Attest:

MICHAEL K. KIRK

*Attesting Officer*     *Acting Commissioner of Patents and Trademarks*